Figure 1:
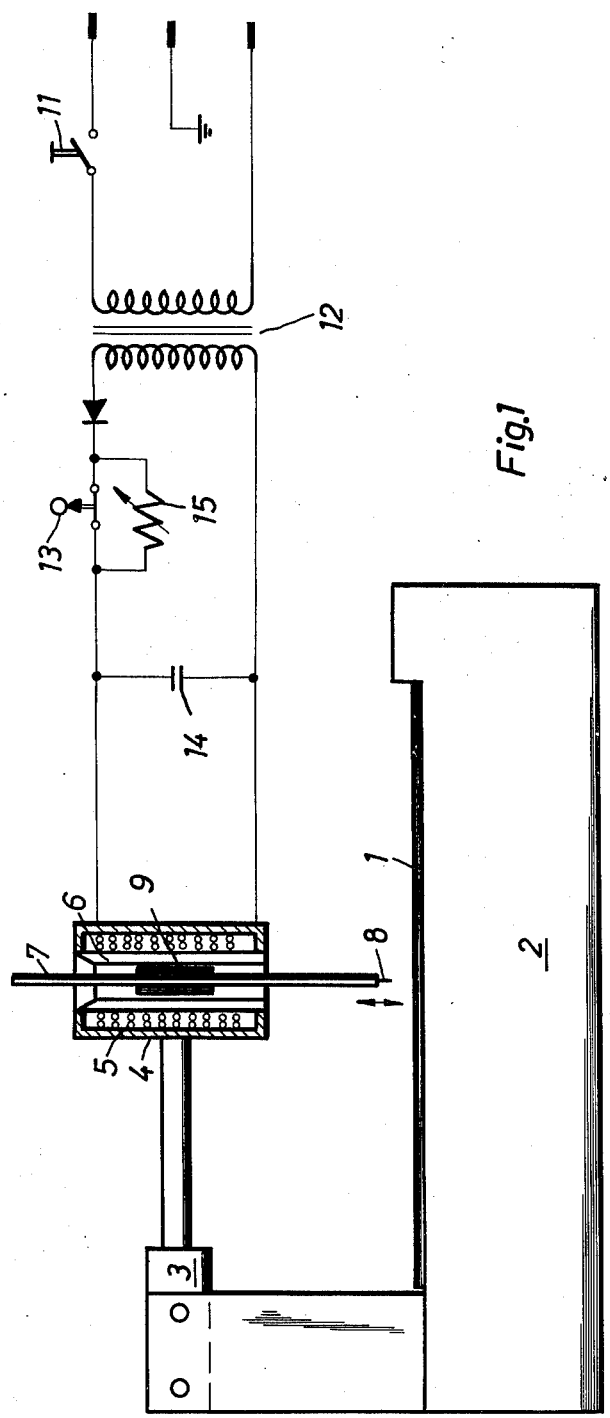

United States Patent [19]

Jänchen

[11] 4,161,508
[45] Jul. 17, 1979

[54] APPARATUS FOR APPLYING LIQUID SAMPLES TO SURFACES

[75] Inventor: Dieter Jänchen, Muttenz, Switzerland

[73] Assignee: Camag Chemie-Erzeugnisse und Adsorptionstechnik AG, Muttenz, Switzerland

[21] Appl. No.: 834,290

[22] Filed: Sep. 19, 1977

[30] Foreign Application Priority Data

Sep. 23, 1976 [DE] Fed. Rep. of Germany ....... 2642777

[51] Int. Cl.² .................. B01L 3/02; G01N 1/12; G01N 31/06; G01N 31/08
[52] U.S. Cl. ................................. 422/100; 422/70; 23/230 B; 73/425.6; 222/160
[58] Field of Search .......................... 23/259, 253 R; 73/423 A, 425.4 P, 425.6; 222/160; 422/100

[56] References Cited

U.S. PATENT DOCUMENTS

| | | | |
|---|---|---|---|
| 3,189,413 | 6/1965 | Davis | 23/253 R |
| 3,234,796 | 2/1966 | Leonards | 73/423 A |
| 3,508,442 | 4/1970 | Lightner et al. | 23/259 X |
| 3,728,079 | 4/1973 | Moran | 23/259 X |
| 3,730,002 | 5/1973 | Penton | 23/259 X |
| 3,900,289 | 8/1975 | Liston | 23/259 X |
| 3,913,636 | 10/1975 | Mochida | 23/259 X |
| 4,070,156 | 1/1978 | Moran | 23/259 X |

Primary Examiner—Michael S. Marcus
Attorney, Agent, or Firm—Gerald J. Ferguson, Jr.; Joseph J. Baker

[57] ABSTRACT

An apparatus for applying liquid samples to surfaces, particularly to the separating layer used in thin-layer chromatography and comparable techniques, consisting of a guided pipette which contains the sample, can be placed on the surface with an adjustable contact pressure and which can be removed therefrom again, the apparatus having an electromagnet, the strength of the magnetic field of which can be adjusted so that it holds the vertically freely movable pipette hovering at the required height in relation to the surface, lifts it away from the surface or allows it to rest on the surface under the influence of the force of gravity.

8 Claims, 4 Drawing Figures

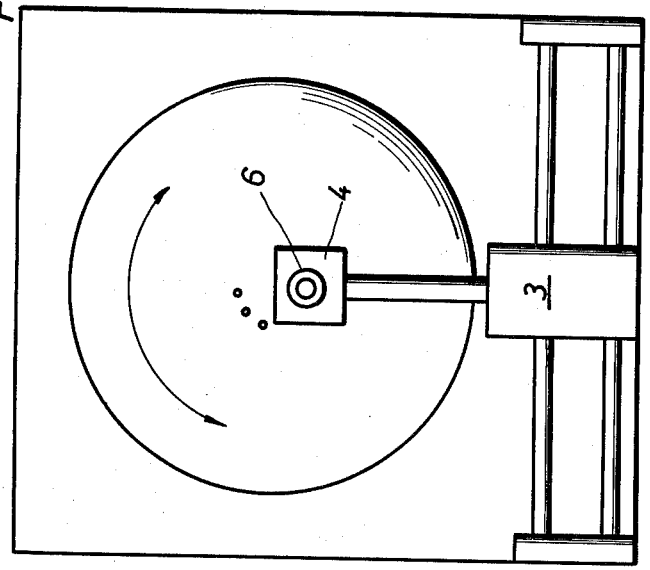
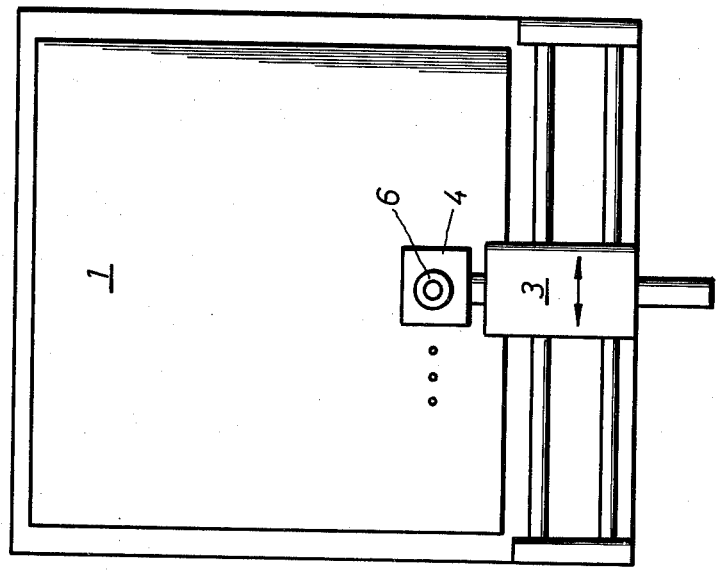

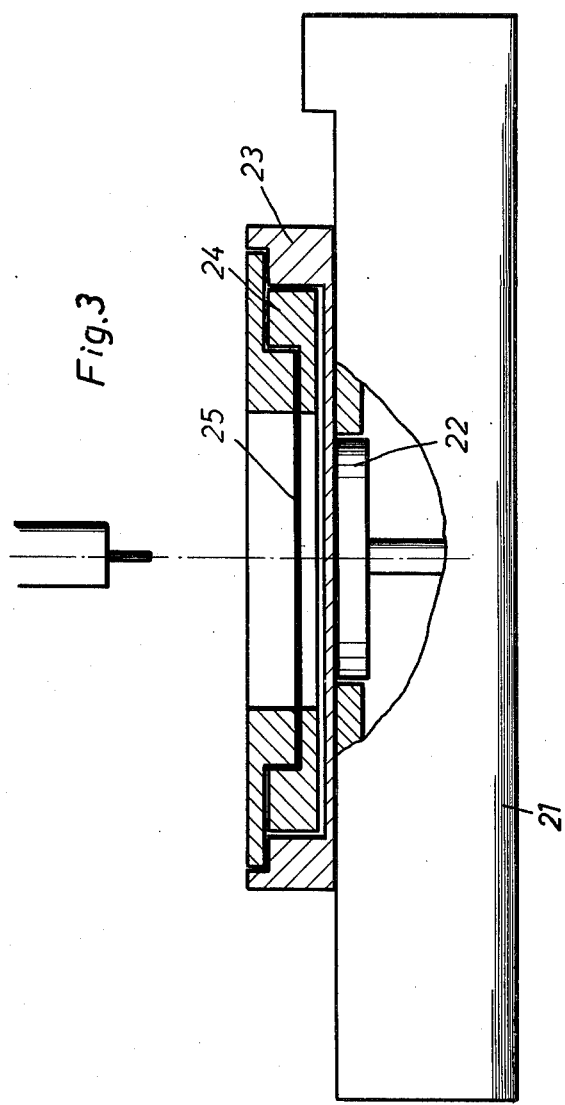

APPARATUS FOR APPLYING LIQUID SAMPLES TO SURFACES

In thin-layer chromatography, paper chromatography, electrophoresis and comparable analytical methods of separation, the necessity arises of applying solutions of the substances to be separated, called samples, to the separating layer. The application of the samples is generally effected in the form of dots but in certain cases it is advisable to apply the samples in the form of lines.

The application of the samples is generally effected by means of pipettes or proportioning syringes but application apparatuses of complicated construction are also used. A method of application which is used particularly frequently consists in that a capillary pipette is placed with its mouth directly on the separating layer. The emptying of the pipette is started by the contact between the column of liquid in the capillary pipette and the absorbent layer and continues until either the entire volume has been absorbed by the layer or the contact between layer and mouth of pipette is interrupted.

Disadvantages of this application of samples consist in that, with layers of granular material, the mouth of the pipette may become blocked, that the layer is damaged, that samples losses may occur as a result of such damage and that the outflow speed of the pipette may depend on the contact pressure, which in turn leads to a series of consequential disadvantages. The effect of all these disadvantages is the greater, the smaller the volume of sample to be applied. The application of amounts of the order of magnitude of a few to a few hundred nanoliters of sample liquid, as is necessary in high-performance thin-layer chromatography (HPTLC), is particularly critical.

In order to avoid these disadvantages, a device has already been proposed wherein the guiding of the capillary pipette is effected via a weight-relieving rocker, wherein the contact pressure can be adjusted as with a gramophone pickup arm by displacing a counterweight on a lever arm. In this device, the fixing of the capillary pipette, which has to be easy to separate from the device, is effected inter alia by magnetic adhesion.

The object of the invention is to provide an apparatus for the application of liquid samples to surfaces which is free of the disadvantages outlined and renders possible a rapid and uniform sample application, for example in dots or lines, without damaging the surface receiving the application.

According to the invention, for this purpose the apparatus has an electromagnet the strength of the magnetic field of which has to be adjusted so that it holds the vertically freely movable pipette suspended at the required height in relation to the surface, lifts it away from the surface or allows it to rest on the surface under the influence of the force of gravity.

By appropriate electrical or electronic switching means, it is possible to divide the emptying of the capillary pipette into intervals in that, after each partial emptying, the pipette is lifted from the surface again. In this manner, it is possible to keep the applied spot of sample smaller than is the case with a single total emptying of the pipette.

Furthermore, it is possible to move the separating medium, for example the thin-layer plate, horizontally in relation to the pipette during the outflow, as a result of which a line of sample is formed. The adjustable contact force of the pipette has a favorable effect.

The drawing shows preferred examples of embodiment of the invention

FIG. 1 shows a side view of one form of embodiment of an apparatus for thin-layer chromatography with parts illustrated in section and with the associated circuit diagram, FIG. 2 shows a plan view of the apparatus of FIG. 1, FIG. 3 shows a side view of the support of the chromatography plate with parts in section in another form of embodiment of the invention and FIG. 4 shows a plan view of the apparatus of FIG. 3.

In the apparatus of FIG. 1, the separating medium, here a thin-layer chromatography plate 1, rests on the lower portion 2 of the device. An electromagnet 5, which is disposed in a housing 4, is suspended on a laterally displaceable arm 3. The electromagnet is so constructed that the magnetic field is formed in the hollow shaft of the coil former. The axial interior of the magnet coil is lined with a material the surface of which has a satisfactory sliding capacity such as polytetrafluoroethylene, glass or the like. This lining 6 is widened out upwards in the form of a funnel to facilitate the introduction of the capillary pipette 7. In a form of embodiment which is preferred for high-performance thin-layer chromatography, the capillary pipette has a metal tip constructed in capillary form, for example a small tube of platinumiridium, stainless steel or the like 8. On its shank, the pipette is provided with a cylindrical iron member 9. The magnetic field of the electromagnet can be adjusted by means of a suitable circuit so that the vertically freely movable iron member 9 either holds the pipette 7 hovering freely at the required height or lifts the pipette 7 from the plate 1 or allows it to rest on the plate 1 under the influence of the force of gravity, at the selected speed in each case. Such a circuit is illustrated diagrammatically in FIG. 1 and contains the following parts.

The primary winding of a transformer 12 is connected to the mains through a switch 11 and its secondary winding feeds the winding of the electromagnet 5 through a circuit comprising a push-button switch 13 and a rectifier, when the push-button switch 13 is closed. The electromagnet 5 is so dimensioned that when the circuit is closed it can hold the iron member 9 with the pipette 7 freely suspended at the required height above the plate.

A capacitor 14 is connected in parallel with the winding of the electromagnet and an adjustable resistor 15 is connected in parallel with the push-button switch 13.

The apparatus is used in the following manner.

After the thin-layer chromatography plate 1 has been placed on the support 2 and the mains switch 11 has been switched on, the capillary pipette 7 is filled outside the apparatus. It is then introduced into the lining 6 of the winding which is widened out at the top in the form of a funnel, and is released. The magnetic field produced when the push-button switch 13 is closed holds the capillary pipette hovering freely above the layer at a distance of a few millimeters. If the push-button switch 13 is opened, the magnetic field of the electromagnet disappears and the pipette rests with its tip 8 on the plate 1, as a result of which the sample is applied. On renewed closing of the push-button switch 13, the iron member 9 with the pipette is again raised into the hovering position. The lowering movement is braked as required and necessary by suitable dimensioning of the capacity of the capacitor 14 and appropriate adjustment of the resistor 15. The pipette is wholly or partially emptied by the contact between the tip of the pipette and the layer. When this has happened, the push-button switch is released and so closed. The magnetic field builds up again and the pipette is restored to its initial position, as already described. The pipette is removed and the next operation of applying a sample can be effected.

As can be seen from FIG. 2, by displacement of the arm, a plurality of samples can be applied in a line as is necessary for normal linear chromatographic development.

With the embodiment shown in FIGS. 3 and 4, samples can be applied to prepare a circular chromatogram.

Here, the lower portion 21 of the device is equipped with a turntable 22, the upper portion 23 of which is constructed so that a standardized plate-holding device 24 can be received therein with sufficient freedom from play. The high-performance thin-layer chromatography plate 25 is in this plate-holding device, for example that of a CAMAG U-chamber. The operation of applying samples is the same as previously described. The electromagnet carrying the pipette is in a variable eccentric position in relation to the turntable, that is to say it is radially adjustable in relation to the turntable.

Apart from this, appropriate forms of embodiment of the apparatus according to the invention may comprise mechanical or electrical means which provide a click-stop arrangement for the lateral feed of the holding arm 3 and of the turntable 22, mechanize the lateral or rotary movement or make the actuation of the electromagnet automatic.

I claim:

1. In an apparatus for applying at least one liquid sample to a separating surface comprising
    electromagnet means having a vertically disposed opening extending therethrough;
    pipette means for containing said liquid sample and being located within said vertically disposed opening, said pipette means being responsive to said electromagnet means and being freely movable within said vertically disposed opening; and
    energizing means for energizing said electromagnet means so that (a) said pipette means is suspended over said surface in response to the electromagnet means being energized, said suspension of the pipette means being effected only by said energizing means and (b) the pipette means falls under the influence of gravity to said surface in response to the energization of said electromagnet means being reduced so that said liquid sample is applied to said surface.

2. Apparatus as claimed in claim 1 including means for horizontally adjusting said electromagnet means and a support for said surface with respect to one another.

3. Apparatus as claimed in claim 1 including means for radially adjusting said surface and a turntable support for the surface with respect to one another.

4. Apparatus as claimed in claim 1 where said energizing means for the electromagnet means includes means for periodically lowering and raising said pipette means.

5. Apparatus as claimed in claim 1 where said energizing means includes means for controlling said reduction of the energization of said electromagnet means to thereby control the fall of said pipette means to said surface under the influence of gravity.

6. Apparatus as claimed in claim 5 where said means for controlling said reduction in the energization of said electromagnet means includes a source of electrical energy connected to said electromagnet means via a switch, a variable resistor connected in parallel with said switch, and a capacitor connected in parallel with the electromagnet means.

7. Apparatus as claimed in claim 1 where said pipette means is freely removable from the upper end of said vertically disposed opening in said electromagnet means so that the pipette can be filled with said liquid sample.

8. Apparatus as claimed in claim 2 where said surface is the surface of a separating layer used in thin-layer chromatography.

* * * * *